US006306366B1

(12) United States Patent
Heldmann et al.

(10) Patent No.: US 6,306,366 B1
(45) Date of Patent: *Oct. 23, 2001

(54) MICROPARTICLES THAT CONTAIN GAS, GALACTOSE AND A SATURATED FATTY ACID

(75) Inventors: Dieter Heldmann; Werner Weitschies; Thomas Fritzsch; Ulrich Speck, all of Berlin (DE)

(73) Assignee: Schering Aktiengesellschaft (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/129,953

(22) Filed: Aug. 6, 1998

Related U.S. Application Data

(62) Division of application No. 08/700,354, filed as application No. PCT/EP95/00484 on Feb. 10, 1995, now abandoned.

(30) Foreign Application Priority Data

Feb. 23, 1994 (DE) .................................................. 44 06 474

(51) Int. Cl.[7] ...................................................... A61B 8/00
(52) U.S. Cl. ............................................................. 424/9.52
(58) Field of Search ................................. 424/9.51, 9.52, 424/9.5

(56) References Cited

U.S. PATENT DOCUMENTS

| 4,832,941 | 5/1989 | Berwing et al. ........................ 424/9 |
| 5,141,738 | * 8/1992 | Rasor et al. ........................... 424/2 |
| 5,147,631 | 9/1992 | Glajch et al. .......................... 424/9 |
| 5,302,372 | 4/1994 | Lin et al. ............................... 424/9 |
| 5,352,436 | 10/1994 | Wheatley et al. ...................... 424/9 |
| 5,380,519 | 1/1995 | Schneider et al. ..................... 424/9 |
| 5,425,366 | 6/1995 | Reinhardt et al. ................... 424/9.52 |
| 5,445,813 | 8/1995 | Schneider et al. .................. 424/9.51 |
| 5,501,863 | 3/1996 | Rössling et al. ..................... 424/489 |
| 5,512,268 | 4/1996 | Grinstaff et al. .................. 424/9.322 |
| 5,540,909 | * 7/1996 | Schutt ................................. 424/9.52 |
| 5,552,133 | * 9/1996 | Lambert et al. ................... 424/9.52 |
| 5,556,610 | 9/1996 | Yan et al. ........................... 424/9.52 |
| 5,558,856 | 9/1996 | Klaveness et al. ................. 424/9.37 |
| 5,558,857 | 9/1996 | Klaveness et al. ................. 424/9.52 |
| 5,567,412 | 10/1996 | Klaveness et al. ................. 424/9.52 |
| 5,569,449 | * 10/1996 | Klaveness et al. ................. 424/9.51 |
| 5,626,833 | * 5/1997 | Schutt et al. ....................... 424/9.52 |

FOREIGN PATENT DOCUMENTS

| 500923 | 4/1990 | (EP) . |
| 365467 | 8/1992 | (EP) . |

OTHER PUBLICATIONS

English Abstract of EP 322,350, Jun. 1989.
English Abstract of EP 122,624, Aug. 1984.
English Abstract of EP 123,235, Oct. 1984.

* cited by examiner

*Primary Examiner*—Michael G. Hartley
(74) *Attorney, Agent, or Firm*—Millen, White, Zelano & Branigan, P.C.

(57) ABSTRACT

Compositions containing microparticles having at least one surface-active substance and at least one non-surface-active solid with a gaseous component containing a halogenated hydrocarbon that is gaseous at body temperature, wherein the gaseous component is more poorly water-soluble than air. Also, ultrasonic contrast media containing such composition, processes for their production, kits for their production and methods of use.

15 Claims, No Drawings

MICROPARTICLES THAT CONTAIN GAS, GALACTOSE AND A SATURATED FATTY ACID

This is a divisional, of application Ser. No. 08/700,354 filed Oct. 21, 1996, now abandoned, which is a 371 of PCT/EP95/00484, filed Feb. 10, 1995.

The invention relates to the object characterized in the claims, i.e., new microparticles that contain gas, diagnostic media that contain the latter, their use in ultrasonic diagnosis as well as process for the production of the particles and media.

Since the discovery by Gramiak at the end of the 1960's that ultrasonic contrasts are caused by small gas bubbles in fluids (blood), the most varied types of gaseous ultrasonic contrast media have been developed and described in the literature.

The simplest type of ultrasonic contrast medium can be produced, e.g., by vigorous shaking, by quick drawing-up in and again squirting out of a hypodermic syringe (so-called "pumping") or irradiation with ultrasound of solutions, such as salt solutions, dye solutions or from blood removed in advance. The small gas bubbles necessary for the echo opacification are introduced in the suspension medium by the previously described methods. Depending on the selection of the medium, a more or less stabilizing effect of the medium on the microgas bubbles can be achieved.

Such contrast media are described, e.g., in EP-0 077 752. Here, mixtures of viscosity-increasing substance and surfactant are used as suspension medium. Air and $CO_2$ are disclosed as gases in EP 0 077 752. The mentioned contrast media as well as similar contrast media that can be produced according to the mentioned methods are affected by the serious disadvantage that the size of the small gas bubbles varies greatly and can be reproduced only poorly, by which a high risk of embolism exists. Further, the small bubbles that are only slightly stabilized by the suspension medium quickly dissolve, so that a contrast effect can be observed only over a short period. A left ventricular contrast after intravenous administration generally cannot be observed with such contrast media.

In WO 93/05819, contrast media based on small bubble emulsions are described, but in which instead of the conventional gases (air, nitrogen, $CO_2$ and noble gases), gases with a specific Q-factor are used. These gases are generally halogenated hydrocarbons. By the use of the latter, it was possible to prolong the contrast effect and especially the duration of the signal. Since the gases also in this case—as already in the case of the previously described contrast media—are introduced, e.g., by recycling several starting substances between two syringes via a three-way cock, into the suspension medium, these media also show a very inhomogeneous distribution of small bubble sizes with the associated risk of embolism.

The use of certain fluorinated substances as gases for various types of ultrasonic contrast media is also claimed in EP 0 554 213. This patent specification also does not relate to the microparticle preparations according to the invention. The closest example (3) of EP 0 554 213 contains microparticles based on galactose [as they are described in EP 0 052 575/Example 1], which contain $SF_6$ instead of air. The effects observed for these particles, however, are weak and only slightly exceed the scattering between the double values of the samples (see Table 3 of EP 0 554 213).

Contrast media with standardized small bubble size are described in EP 0 122 624 and 0 123 235. These contrast media consist of gas-containing microparticles. As particle material, mixtures of surface-active substances, such as, e.g., fatty acids and non-surface-active substances, such as, e.g., saccharides, are used; air is disclosed as gas. These media specifically show the desired standardization relative to the small bubble size, but the small gas bubbles dissolve relatively quickly in the blood plasma, so that the diagnostic time window is small.

Similar contrast media are disclosed in EP 0 365 467. The latter, after i.v. administration of the medium, survive the passage of the pulmonary capillary bed and are thus suitable for the contrasting of the left ventricle and the arterial blood. For a sufficiently long and intensive contrast effect, however, the latter must be administered, as also the contrast media described in EP 0 122 624 and 0 123 235, at a concentration that is not blood-isotonic, which can result in known irritations in patients.

Other ultrasonic contrast media with standardized small bubble size are disclosed in DE 38 03 972 and EP 0 441 468 as well as in DE 38 03 972 and EP 0 357 163. The two first-mentioned patent specifications describe microparticles for ultrasonic diagnosis in which the imaging substances (gases or low-boiling organic liquids) are present in encapsulated form. As shell material, polycyanacrylates (DE 38 03 972) or polymerized aldehydes (EP 0 441 468) are used. The last-mentioned patent specifications describe microparticles in which the gases (or low-boiling organic liquids) are present in complex form (i.e., in the form of a host/guest complex). Although in these patent specifications halogenated hydrocarbons (such as, e.g., bromomethane or dibromodifluoromethane) or in the case of EP 0 357 163 and EP 0 441 468, sulfur hexafluoride, are also disclosed as gases or low-boiling liquids in addition to the usual substances, such as air, nitrogen, no or only a slight effect of the enclosed imaging components on the contrast intensity or period is observed or described for ultrasonic contrast medium preparations that are prepared from these microparticles.

The object of this invention was therefore to provide a contrast medium with defined small bubble size for ultrasonic diagnosis, which, after intravenous administration, is able to achieve long-term contrast effects in the blood and to make its flow conditions on the right and left ventricular sides visible for ultrasound. In particular, the contrast medium should already be able to achieve contrasting that can be evaluated diagnostically in a dose range in which the medium is largely blood-isotonic.

Moreover, the other requirements to be set for an in-vivo contrast medium should also be met. In addition to good compatibility, especially a wide spectrum of use is desired for a modern contrast medium, thus it should also be suitable for the visualization of the blood flow of other organs or tissues, such as, e.g., the myocardium, liver, spleen, kidneys and brain, or after peroral or rectal administration also for the visualization of the gastrointestinal tract. After administration in the bladder, a visualization of the urinary flow should also be possible, such as a contrasting of the tubes after intrauterine administration. The contrast medium should also be universally usable in the various sonographic modes (e.g,, B-mode, Doppler, "Harmonic Imaging").

This object is achieved by this invention.

It has been found that microparticles that consist of the mixture of at least one surface-active substance with at least one non-surface-active substance and a component that is gaseous at body temperature, characterized in that a substance or a substance mixture is contained as a gaseous component, which is (are) more poorly water-soluble than air, meet the set requirement profile and are therefore extremely well suited as contrast media in ultrasonic diagnosis.

The ultrasonic contrast media obtained by suspending the microparticles according to the invention in a liquid vehicle result especially in—in comparison to the known prior art—surprisingly intensive and long-term contrasting. As a result, the dose necessary for imaging can be reduced by 90% and more relative to the contrast media that are disclosed in BP 0 365 467 (see also Example 18). in this way, contrast media can be obtained that are blood-isotonic or almost blood-isotonic, by which the compatibility is clearly increased. Based on the long-term contrast effects, the media according to the invention are especially suitable also as "blood pool agents."

As surface-active substances, there are phospholipids, sterols, glycolipids, saccharose esters, such as, e.g., soybean oil saccharose glycerides, saturated or unsaturated fatty acids or their salts, fatty alcohols, mono-, di- and triglycerides, fatty acid esters, such as, e.g., butyl stearate, xyloglycerides, such as, e.g., palm oil xylide, polyethoxylated sorbitan fatty acid esters, such as, e.g., polyethylene glycol sorbitan monostearate, polyoxyethylene fatty acid esters, polyoxyethylene fatty acid ethers, polyoxyethylenes, polyoxyethylene-polyoxypropylene block polymers, ethoxylated or sulfated fatty alcohols, alkylarylpolyether alcohols, fluorinated fatty alcohols, ethoxylated or sulfated fluorinated fatty alcohols, fluorinated alkylakoxylates, whereby saturated $C_{12}$–$C_{26}$ fatty acids such as palmitic acid, polyoxyethylene-polyoxypropylene block polymers and ethoxylated fluorinated $C_{14}$–$C_{30}$ fatty alcohols are preferred. The microparticles according to the invention contain the surface-active substances at a concentration of up to 10%, preferably at a concentration of 0.001 to 5%, especially at a concentration of 0.01 to 1%.

As non-surface-active solids, both water-soluble solids and cyclodextrins, such as, e.g., α-, β-, γ-cyclodextrins, their monomeric, oligomeric or polymeric derivatives, monosaccharides, such as, e.g., glucose, fructose, galactose, oligosaccharides, such as, e.g., saccharose, lactose, maltose, arabinose, xylose, ribose, polysaccharides, such as, e.g., dextran, starch or starch derivatives, degradation products of starches, such as, e.g., dextrins and/or inorganic or organic salts, such as, e.g., sodium chloride, sodium citrate, sodium phosphate, sodium acetate or sodium tartrate as well as salts of triiodized benzoic acids (amidotrizoate) or nonionic triiodine compounds (iopromide), just as salts of complexes of rare earths (Gd-DTPA) and water-insoluble substances, such as clay particles, iron oxide particles or insoluble particles of plant origin with a particle diameter of less than 500 μm, preferably less than 100 μm, are suitable. Whereby for intravenous use, preferably soluble particles with a particle size that is less than 10 μm are used. Especially preferred for intravenous administration are water-soluble particles from monosaccharides, especially galactose or disaccharides such as lactose as well as particles from α- and hydroxypropyl-β-cyclodextrin. For peroral or rectal administration, in addition to the soluble particles, preferably insoluble particles, especially clay particles as well as particles of plant origin, are used.

The microparticles according to the invention contain the non-surface-active solids at a concentration of at least 90%, preferably at a concentration of 95% by weight.

As in the case of halogenated compounds that are gaseous at body temperature (abbreviated as "gas" below), tetrafluoroallenes, hexafluoro-1,3-butadiene, decafluorobutane, perfluoro-1-butene, perfluoro-2-butene, perfluoro-2-butine, octafluorocyclobutane, perfluorocyclobutene, perfluorodimethylamine, hexafluoroethane, tetrafluoroethylene, pentafluorothio(trifluoro)methane, tetrafluoromethane, perfluoropentane, perfluoro-1-pentene, perfluoropropane and/or perfluoropropylene are suitable. According to the invention, hexafluoroethane, decafluorobutane and/or perfluoropropane are preferred.

Up to isomolar amounts of nitrogen can optionally also be admixed with the above-mentioned fluorinated gases.

The particles according to the invention can be produced in varied ways. They can be obtained, e.g., by the particles that are disclosed in EP 0 365 467, EP 0 122 624, EP 0 123 235 or in EP 0 500 023, EP 0 543 020, EP 0 525 199, U.S. Pat No. 5,107,842 being treated with the previously mentioned gases to achieve an exchange of the gas contained in the particles (generally air) for the desired halogenated compounds. This gas exchange takes place advantageously by the respective particles being introduced in a corresponding vessel, which is then evacuated and subsequently aerated with the desired gas. The incubation can also be carried out directly in the vials, in which the particles get to the user. In principle, the gas exchange can also be carried out at any other point of the production process. Thus the possibility exists, especially in the case of the particles of EP 0 365 467, EP 0 122 624, EP 0 123 235, to introduce the gas during the crushing process, i.e., in the case of grinding, e.g., in an "air-jet mill" operated with the desired gas. The atmosphere of the desired gas is preferably to be maintained in subsequent production steps.

In addition to the previously described gas exchange that is performed later, however, the gas can also be introduced as early as during the particle production. In this case, the procedure is advantageously analogous to the methods that are described in EP 0 365 467, EP 0 122 624 or EP 0 123 235, whereby all reaction solutions are saturated with the desired halogenated gas in advance and the entire production is performed under an atmosphere of the desired halogenated gas.

A variant of the previously described process exists in that first only the non-surface-active substance is recrystallized under sterile conditions from a solution that is saturated with the desired gas. Then, the surface-active substance together with the non-surface-active solid is mixed (agglomerated) under sterile conditions under the atmosphere of the desired halogenated gas and crushed until the desired particle size of <10 µm, preferably <8 µm, especially 1–3 µm, is achieved. The particle size is determined in suitable measuring devices.

An alternative process for the production of the microparticles according to the invention consists in dissolving the particles, described in EP 0 365 467, EP 0 122 624 or EP 0 123 235, in a suitable medium that is saturated with the desired halogenated gas and in recrystallizing them from the latter. Drying, crushing, filling, etc., are carried out as previously described, whereby all downstream production steps advantageously are performed under an atmosphere of the respective gas.

From the microparticles according to the invention, the media according to the invention can easily be produced by suspending the particles in a suitable physiologically compatible medium. The suspending is carried out—especially in the case of the soluble particles—advantageously only immediately before the injection by the attending physician, by the suspension medium being removed from a first container under sterile conditions, e.g., by means of a syringe, being added to the microparticles that are contained in a second container and then a homogenous suspension being produced by brief (5- to 10-second) vigorous shaking of the combined components. The media according to the invention are injected immediately after their production, but at the latest within 5 minutes, either as a bolus in a peripheral vein or in a previously placed catheter.

The invention therefore also relates to a kit for the production of an ultrasonic contrast medium that contains microparticles and gas and that consists of a first container, provided with a closure, that makes possible the removal of the contents under sterile conditions and is filled with the liquid suspension medium, and a second container, provided with a closure, that makes possible the adding of suspension medium under sterile conditions, filled with the microparticles according to the invention and a gas or gas mixture which is identical to the gas contained in the microparticles, whereby the volume of the second container is dimensioned in such a way that the suspension medium of the first container has plenty of room in the second container.

Instead of two separate containers, of course, a prefilled syringe that consists of two chambers, one of which contains the suspension medium and the other of which contains the particles, can also be used.

As physiologically compatible suspension media, water, aqueous solutions of one or more inorganic salts, such as physiological common salt solution, and buffer solutions, aqueous solutions of mono- or disaccharides, such as galactose, glucose or lactose, or cyclodextrins, monovalent or multivalent alcohols, in so far as they are physiologically compatible, e.g., ethanol, polyethylene glycol, ethylene glycol, glycerol, propylene glycol, propylene glycol methyl ester, are suitable. Preferred are water and physiological electrolyte solutions, such as, e.g., physiological common salt solution as well as aqueous solutions of galactose and glucose. The concentration of the dissolved substances is 0.1 to 30% by weight, preferably 0.5 to 25% by weight.

As a suspension medium for microparticles of inorganic materials, the previously mentioned ones are suitable, whereby it has proven advantageous to add a hydrocolloid, such as, e.g., pectin, to the medium. Such media are suitable especially for contrasting the gastrointestinal tract.

Of course, different pharmaceutical adjuvants and stabilizers can be added to the media. The indicated measurements and percentages are also meant as guide values. Exceeding them or falling short of them can be possible and beneficial in individual cases.

Depending on use, the media according to the invention contain 5 mg to 500 mg of particles per ml of suspension medium. The small gas bubbles that are required for opacification are transported by the microparticles. The latter are partially adsorbed on the surfaces of the microparticles or enclosed in the gaps between the microparticles or by the intercrystalline pathway.

For intravenous applications, only media based on soluble particles are used, moreover, media based on insoluble particles can also be used for peroral or rectal application. As a function of the use, the respectively administered dose also varies, thus in the case of intravenous administration, generally 0.01 ml to 1 ml/kg of body weight is administered; in the case of peroral administration, 1 to 30 ml/kg of body weight is administered.

After intravenous administration, the ultrasonic contrast media according to the invention reach the left ventricular side and are thus also extremely well suited for contrasting other organs that are supplied with blood from the aorta, such as myocardium, liver, spleen, kidneys, i.a. It goes without saying that the ultrasonic contrast media according to the invention also are suitable for contrasting the right ventricle and other organs and regions of the body.

A completely surprising advantage of the media according to the invention lies in the possibility of an extraordinarily great dose reduction in comparison to the media of the prior art, by which it is possible to reduce the substance load, the volumes to be administered or the osmolarity of the media. Thus, ultrasonic contrast media that are blood-isotonic or almost blood-isotonic can also be made available. Another advantage is high resistance to irradiated ultrasonic waves, which leads to considerably improved intravital stability.

The following examples are used for a more detailed explanation of the object of the invention, without intending that they be limited to this object.

EP 365,467

EXAMPLE 1

A) Carrier Liquid
  Water for Injection Purposes
B) Production of Microparticles
  I 1998 g of galactose is purified in 1080 g of water, dissolved, sterilized by filtration and cooled under aseptic conditions to 8–10° C.,
  II 2 g of palmitic acid is dissolved in 120 g of ethanol, sterilized by filtration and I is added while being stirred.
  III The combined solutions are brought to a dry state under aseptic conditions at about 40° C. and an under pressure of 50 mbar.

IV The recrystallizate is crushed under aseptic conditions with a compressed-air mill to the following grain size distribution:

$D_{10} \leq 1\ \mu m$
$D_{50} \leq 2.6\ \mu m$
$D_{50} \leq 5\ \mu m$

The determination of the grain size distribution is done with a particle measuring device (e.g., Cilas granulometer 716) after the micronizate is suspended in alcohol.

V The packaging of the microparticles, 3 g in each case, is carried out in 20 ml vials.

C) Production of Ready-to-Use Ultrasound Contrast Medium 8.5 ml of water is transferred for injection purposes using a hypodermic syringe into the 20 ml vial that contains 3 g of microparticles, and it is shaken until a homogeneous suspension is produced (5–10 seconds).

EP 123,235

EXAMPLE 2

A. Production of the Carrier Liquid

Water for injection purposes, in each case 4 ml, is decanted into 5 ml vials and sterilized for 20 minutes at 120° C.

B. Production of Microparticles

Under sterile conditions, a solution of 0.5 g of soybean oil saccharose glyceride in 40 g of isopropanol that is sterilized by filtration is taken up on 199.5 g of sterile galactose particles, the isopropanol is dried at 40° C. and 200 torr and ground with a compressed-air mill until the following size distribution of the particles is produced:

Median value 1.9 $\mu m$
min. 99% <6 $\mu m$
min. 90% <3 $\mu m$.

The determination of the size of the particles and their distribution is carried out in a particle measuring device, e.g., after suspension in isopropanol. 2 g of the microparticles is packed in 5 ml vials in each case.

C. For the production of 5 ml of ready-to-use ultrasound contrast medium, the contents of a vial with carrier liquid (water for injection purposes, A) are added via a hypodermic syringe into the vial with microparticles (B) and shaken until a homogeneous suspension is produced (5 to 10 seconds).

EP 123,325

EXAMPLE 3

A. Production of the Carrier Liquid 4.5 g of sodium chloride is dissolved in water until volumes of 500 ml are produced, the solution is forced through a 0.2 mm filter, in each cases 4 ml of this solution is loaded into 5 ml vials and sterilized for 20 minutes at 120° C.

B. Production of Microparticles

Under sterile conditions, a solution of 0.5 g of polyethylene glycol sorbitan monostearate in 40 g of isopropanol that is sterilized by filtration is taken up on 199.5 g of sterile galactose particles, the isopropanol is dried at 40° C. and 200 torr and ground with a compressed-air mill until the following size distribution of the particles is produced:

Median value 1.9 $\mu m$
min. 99% <6 $\mu m$
min. 90% <3 $\mu m$.

The determination of the size of the particles and their distribution is carried out in a particle measuring device, e.g., after suspension in isopropanol. 2 g of the microparticles is packed in 5 ml vials in each case.

C. For the production of 5 ml of ready-to-use ultrasound contrast medium, the contents of a vial with carrier liquid (water for injection purposes, A) are added via a hypodermic syringe into the vial with microparticles (B) and shaken until a homogeneous suspension is produced (5 to 10 seconds).

EP 123,325

EXAMPLE 4

A. Production of the Carrier Liquid 4.5 g of sodium chloride is dissolved in water until volumes of 500 ml are produced, the solution is forced through a 0.2 mm filter, in each case 4 ml of this solution is loaded into 5 ml vials and sterilized for 20 minutes at 120° C.

B. Production of Microparticles

Under sterile conditions, a solution of 0.5 g of palm oil xylite in 40 g of isopropanol that is sterilized by filtration is taken up on 199.5 g of sterile galactose particles, the isopropanol is dried at 40° C. and 200 torr and ground with a compressed-air mill until the following size distribution of the particles is produced:

Median value 1.9$\mu$
min. 99% <6 $\mu m$
min. 90% <3 $\mu m$.

The determination of the size of the particles and their distribution is carried out in a particle measuring device, e.g., after suspension in isopropanol. 2 g of the microparticles is packed in 5 ml vials in each case.

C. For the production of 5 ml of ready-to-use ultrasound contrast medium, the contents of a vial with carrier liquid (water for injection purposes, A) are added via a hypodermic syringe into the vial with microparticles (B) and shaken until a homogeneous suspension is produced (5 to 10 seconds).

EP 500,023

EXAMPLE 1

An image agent was prepared from sterile water, citrus pectin, and purified edible kaolin, the citrus pectin was water-soluble and the kaolin had an average particle size of rom 1 to 2 microns. A premeasured amount of water, such as 500 ml, was added to a Waring blender, and 2.5 grams of kaolin and 2.5 grams of the pectin was added per each 100 ml water. The kaolin can be added first and then the pectin. The blender was turned on to a low speed pulse so that the mixture was blended for at least 10 seconds. The resulting mixture was manually stirred and blended again with the full speed pulse of the blender for at least an additional 10 seconds. The viscosity of the mixture is measured at around 1200 centipoises. The resulting dispersion is then poured through several layers of U.S.P. Gause and then degassed for a minimum of half an hour. A final viscosity measurement is made to determine if the viscosity is as desired.

The imaging agent thus prepared as described was administered orally to several subjects for ultrasonic imaging of the stomach and upper colon. Observations made during the abdominal ultrasound imaging are summarized as follows:

(1) Precontrast: This was variable from individual to individual, or for a single individual form one day to another, but gas present in the abdomen is not an unusual occurrence. For individuals without a substantial amount of gas, the stomach can be visualized, but the lining of the stomach wall is not well delineated. The pancreas may be imaged, but, in general, the image quality is poor and just the tail portion is observed.

(2) During Administration: Subjects imaged had fasted for a minimum of nine hours prior to examination. Subjects drank approximately 100–200 ml of the above-described contrast agent dispersion. Imaging was essentially continuous from the precontrast time, through the administration, and until the postcontrast visualization was completed.

(3) Postcontrast: As the dispersion entered the stomach, a concentrated bright clump appeared so that a homogeneous contrast was observed in the stomach cavity. In response to the ingestion, the stomach dilated. The contrast in the stomach was very homogeneous and did not contain individual, bright, specular reflectors. The contrast material remained in the stomach for a period of time depending on the viscosity: very quickly (1–2 minutes) for low viscosity solutions (25 to 75 centipoise), and longer (up to 20 minutes) for higher viscosity solutions (200 to 1000 centipoise). As stomach motility occurred, the contrast agent moved within the stomach, giving delineation of the stomach wall. As the contrast material is seen to move out of the stomach, visualization of the pyloric valve and duodenum was provided. Although the stomach then had an empty interior, the lining of the stomach remained coated with the clay particle sound reflectors which gave very good visualization of the wall lining. This effect lasted for some time after the stomach appeared empty (viz. up to 60 minutes). Beginning with the contrast agent entering the stomach, the gas was displaced and there was visualization of structure hidden by the stomach, especially the pancreas. As the contrast material passed out of the stomach and on to farther GI structures, the head of the pancreas was visualized.

In a comparable abdominal imaging with a contrast agent that did not contain any pectin, but only kaolin, revealed that the contrast agent did not persist in the stomach and did not coat the stomach lining. The kaolin only contrast agent did not displace bowel gas and did not improve visualization of structures proximal to the stomach. Abdominal imaging with a contrast agent that does not contain any kaolin, but only pectin, revealed that the contrast agent did not provide homogeneous scatterers (the clay particles) within the stomach, and after the agent had left the stomach, the lining of the stomach was not enhanced.

Summarizing, by the use of the contrast agents and method of this invention there is created an improved acoustic window through the stomach to identify structures hidden by the stomach, e.g., pancreas. This effect is achieved by the removal of intestinal gas and the delineation of structures. At the same time, the coated walls were partially transparent to the ultrasonic waves.

Example 1

Microparticles that are produced according to Example 1 of EP 0 365 467 reproduced above are filled to 2 g in 20 ml vials. The filling is carried out under an atmosphere of hexafluoroethane, which also is contained in the vials.

Example 2

Microparticles that are produced according to Example 1 of EP 0 365 467 reproduced above are filled to 2 g in 20 ml vials. The filling is carried out under an atmosphere of decafluorobutane, which also is contained in the vials.

Perfluoropropane-containing particles can be obtained analogously to Example 2, by the vial being filled under an atmosphere of perfluorobutane.

Example 3

Microparticles that are produced according to Example 3 of EP 0123 235 reproduced above are stored for 24 hours in an atmosphere of hexafluoroethane (normal pressure). The microparticles are then filled in amounts of 2 g in 20 ml vials under an atmosphere of hexafluoroethane.

Example 4

Microparticles that are produced according to Example 4 of EP 0 123 235 reproduced above are stored for 24 hours in an atmosphere of an isomolar mixture of hexafluoroethane and decafluorobutane. The microparticles are then filled in amounts of 2 g in 20 ml vials under an isomolar atmosphere of hexafluoroethane and decafluorobutane.

Example 5

Microparticles that are produced according to Example 1 of EP 0 365 467 reproduced above are filled to 3 g in 20 ml vials. The filling is carried out under an atmosphere of hexafluoroethane, which also is contained in the vials.

Example 6

Microparticles that are produced according to Example 2 of EP 0 123 235 reproduced above are filled to 3 g in 20 ml vials. The filling is carried out under an isomolar atmosphere of decafluorobutane and hexafluoroethane, which also is contained in the vials.

Example 7

Microparticles that are produced according to Example 3 of EP 0 123 235 reproduced above are filled to 3 g in 20 ml vials. The filling is carried out under an atmosphere of hexafluoroethane.

Example 8

Contrast medium according to Example 1 of EP 0 500 023 reproduced above was incubated for 24 hours in an atmosphere of hexafluoroethane before administration.

Example 9

Microparticles are produced according to Example 3 of EP 0 123 235 reproduced above. The grinding in the air-jet mill is carried out, however, under hexafluoroethane atmosphere.

Example 10

Microparticles are produced analogously to the process described in EP 0 123 235/Example 3, reproduced above whereby the solvents (ethanol or water) for the surface-active substance and the non-surface-active substance were supersaturated with decafluorobutane in advance. Filling and storage also are carried out under a decafluorobutane atmosphere.

Example 11

Microparticles that are produced according to Example 1 of EP 0 365 467 reproduced above are stored in open vials in a container that can be evacuated and are evacuated in it up to a pressure of 50 mbar. Then, the container is aerated with hexafluoroethane, and the vials are sealed under a hexafluoroethane atmosphere.

Example 12

The procedure is analogous to Example 11, whereby decafluorobutane instead of hexafluoroethane is used as gas.

Example 13

The procedure is analogous to Example 11, whereby perfluoropropane instead of hexafluoroethane is used as gas.

Example 14

The procedure is analogous to Example 11, whereby perfluoropentane instead of hexafluoroethane is used as gas.

Example 15

1997 g of galactose is dissolved in 1080 g of water and cooled to 5° C. 3 g of lignoceric acid, which previously was dissolved in 120 g of ethanol, is added to the suspension that is produced while being stirred. The suspension is then dried at 40° C. and a partial vacuum of 50 mbar. The product that is produced is crushed with an air-jet mill to a particle size of $d_{(99\%)} < 8$ $\mu$m. The microparticles are agglomerated to a granulate and filled in portions of 2 g each in a 20 ml vial, evacuated, gassed with decafluorobutane, incubated for 24 hours in decafluorobutane atmosphere and then sealed.

Example 16
(In Vivo Test)

4 g of a preparation that is produced according to Example 8 is resuspended as a diluent with 250 ml of a it aqueous pectin solution and administered perorally to a sedated beagle (11 kg of body weight). (The animal was not fed within 24 hours before the test). After intensive contrasting of the stomach, a lasting increase of echogeneity in the lumen of the bowels is achieved.

Example 17
(In Vivo Comparison Example)

A) 1 g of the microparticles, according to the invention, produced according to Example 5 was suspended in 2.7 ml of water p.i. 2 ml of the freshly prepared suspension was intravenously injected in an anesthetized beagle (10 kg of body weight) and the heart was examined with an ultrasound device. The course of the contrast in the left ventricle was recorded by videodensitometry and evaluated.

B) 1 g of microparticles produced according to Example 1 of EP 0 365 467 reproduced above was suspended in 2.7 ml of water p.i. 2 ml of the freshly prepared suspension was intravenously injected in an anesthetized beagle (10 kg of body weight) and the heart was examined with an ultrasound device. The course of the contrast in the left ventricle was recorded by videodensitometry and evaluated. All other test parameters remained unchanged relative to test A).

Result: The injection of the contrast medium preparation according to the invention results in clearly more intensive and clearly longer-lasting contrast ("blood pool agent").

Example 18
(In Vivo Comparison Test)

For comparison purposes, contrast medium preparations are freshly prepared from

A) microparticles produced according to Example 1 of EP 0 365 467 reproduced above and B) microparticles, according to the invention, produced according to Example 12. Water p.i. is used as suspension medium. 1 ml of the respective suspension is intravenously injected in the anesthetized beagle (10 kg of body weight) directly after preparation, and the heart was examined with an ultrasound device. The course of the ultrasonic contrast enhancement in the left ventricle of the heart is recorded by videodensitometry and evaluated. The observed data (average values of 3 tests each) are compiled in the table below.

| Type of Particle | Concentration | Dose per Animal (mg) | Contrast Intensity (DU) | Contrast Intensity (Relative) |
|---|---|---|---|---|
| EP 0 365 467/ Example 1 | 300 mg/ml | 300 | 58 | 100 |
| Particles of the invention according to Example 12 | 50 mg/ml | 50 | 90 | 155 |

Result: In a dose reduction by a factor of 6, the contrast media according to the invention themselves show an even more intensive contrast than the media of EP 0 365 467. The blood isotonicity of the preparation according to the invention is very advantageous compared to the hypertonic preparation according to Example 1 of EP 0 365 467.

Example 19
(In Vivo Comparison Test)

Additional data from a comparison test that is performed analogously to Example 18 are compiled in the table below.

| Type of Particle | Concentration | Dose per Animal (mg) | Contrast Intensity (Relative) |
|---|---|---|---|
| EP 0 365 467/ Example 1 | 300 mg/ml | 600 | 100 |
| Particles of the invention according to Example 12 | 12.5 mg/ml | 25 | 196 |
| | 6 mg/ml | 12 | 160 |
| | 3 mg/ml | 6 | 145 |

Also in this case, when using the contrast medium preparation according to the invention despite a dose reduction by up to a factor of 100, a more intensive contrast than when using the contrast medium preparation according to example 1 of EP 0 365 467 can be observed.

What is claimed is:

1. A composition for the preparation of an ultrasonic contrast medium which comprises microparticles that comprise a mixture of galactose and at least one saturated $C_{12}$–$C_{26}$ fatty acid and at least one of perfluoropropane, perfluorobutane or hexafluoroethane which is gaseous at body temperature and more poorly water-soluble than air.

2. The composition of claim 1, wherein the microparticles contain the saturated $C_{12}$–$C_{26}$ fatty acid in a concentration of 0.01 to 10% by weight and galactose in a concentration of 90 to 99.99% by weight.

3. The composition of claim 1, wherein the saturated $C_{12}$–$C_{26}$ fatty acid is palmitic acid.

4. An ultrasonic contrast medium which comprises the composition of claim 1 in a physiologically compatible liquid suspension medium.

5. The ultrasonic contrast medium of claim 4, wherein the physiologically compatible liquid suspension medium is water, a physiological electrolyte solution, an aqueous solution of at least one monovalent or multivalent alcohol or an aqueous solution of a mono- or di-saccharide.

6. A kit for the production of an ultrasonic contrast medium that contains microparticles and gas and that consists of a) a first container, provided with a closure, that makes possible the removal of the contents under sterile conditions and is filled with a physiologically compatible liquid suspension medium and b) a second container, provided with a closure, that makes possible the adding of the suspension medium under sterile conditions, containing a composition according to claim 1, whereby the volume of the second container is dimensioned in such a way that the suspension medium of the first container can be completely contained in the second container.

7. A process for the production of a contrast medium that contains microparticles and gas for ultrasonic diagnostic, which comprises combining a composition according to claim 1 with a physiologically compatible carrier liquid and shaking the combination until a homogenous suspension develops.

8. A process for the production of a composition according to claim 1, wherein:

a) galactose, dissolved in water, is recrystallized with the addition of an alcoholic solution of the $C_{12}$–$C_{26}$ fatty acid while being stirred, whereby the respective solutions are saturated with perfluoropropane, perfluorobutane or hexafluoroethane gas, or b) microparticles that consist of at least 90% by weight of galactose and 0.01 to 10% by weight of the $C_{12}$–$C_{26}$ fatty acid are fed under a pressure of 1 to 30 atmospheres for from 1 hour to 6 days with perfluoropropane, perfluorobutane or hexafluoroethane gas, whereby optionally other gases are removed in advance by evacuation, or c) microparticles that consist of at least 90% by weight of galactose and 0.01 to 10% by weight of the $C_{12}$–$C_{26}$ fatty acid are ground in an air-jet mill, operated with perfluoropropane, perfluorobutane or hexafluoroethane gas and then is ground under an atmosphere of said gas with the $C_{12}$–$C_{26}$ fatty acid, or d) microparticles that consist of at least 90% by weight of galactose and 0.01 to 10% by weight of the $C_{12}$–$C_{26}$ fatty acid substance are dissolved in a medium that is saturated with perfluoropropane, perfluorobutane or hexafluoroethane gas and then are recrystallized from the medium.

9. The kit of claim 6, wherein the saturated $C_{12}$–$C_{26}$ fatty acid is palmitic acid.

10. A composition for the preparation of an ultrasonic contrast medium that is blood-isotonic or substantially blood-isotonic which comprises microparticles that comprise a mixture of galactose and at least one saturated $C_{12}$–$C_{26}$ fatty acid and at least one of perfluoropropane, perfluorobutane or hexafluoroethane which is gaseous at body temperature and more poorly water-soluble than air.

11. A composition for the preparation of an ultrasonic contrast medium which comprises microparticles in a liquid suspension medium at a concentration of 3–50 mg of microparticles per ml of liquid suspension medium, wherein said microparticles comprise a mixture of galactose, at least one saturated $C_{12}$–$C_{26}$ fatty acid and at least one of perfluoropropane, perfluorobutane or hexafluoroethane which is gaseous at body temperature and more poorly water-soluble than air.

12. The composition of claim 10, wherein the microparticles contain the saturated $C_{12}$–$C_{26}$ fatty acid in a concentration of 0.01 to 10% by weight and galactose in a concentration of 90 to 99.99% by weight.

13. The composition of claim 10, wherein the saturated $C_{12}$–$C_{26}$ fatty acid is palmitic acid.

14. The composition of claim 11, wherein the microparticles contain the saturated $C_{12}$–$C_{26}$ fatty acid in a concentration of 0.01 to 10% by weight and galactose in a concentration of 90 to 99.99% by weight.

15. The composition of claim 11, wherein the saturated $C_{12}$–$C_{26}$ fatty acid is palmitic acid.

* * * * *